United States Patent [19]

Neuenschwander et al.

[11] Patent Number: 4,904,691
[45] Date of Patent: Feb. 27, 1990

[54] NOVEL HMG-COA REDUCTASE INHIBITORS

[75] Inventors: Kent W. Neuenschwander, Ambler; Anthony C. Scotese, King of Prussia, both of Pa.

[73] Assignee: Rorer Pharmaceutical Corporation, Fort Washington, Pa.

[21] Appl. No.: 321,950

[22] Filed: Mar. 10, 1989

Related U.S. Application Data

[63] Continuation-in-part of Ser. No. 135,805, Dec. 21, 1987, Pat. No. 4,863,957.

[51] Int. Cl.$^4$ .................. A61K 31/365; C07D 309/30
[52] U.S. Cl. .................................... 514/449; 514/460; 514/824; 549/264
[58] Field of Search ............... 549/264, 292; 514/460, 514/459, 824

[56] References Cited

U.S. PATENT DOCUMENTS

| | | | |
|---|---|---|---|
| 4,282,155 | 8/1981 | Smith et al. | 549/292 |
| 4,308,378 | 12/1981 | Stokker | 549/292 |
| 4,503,072 | 3/1985 | Hoffman et al. | 549/292 |
| 4,567,289 | 1/1986 | Willard et al. | 560/59 |
| 4,611,067 | 9/1986 | Volante et al. | 556/292 |
| 4,622,338 | 11/1986 | Boran et al. | 549/292 |
| 4,668,699 | 5/1987 | Hoffman et al. | 560/119 |
| 4,681,893 | 7/1987 | Roth | 514/423 |
| 4,772,626 | 9/1988 | Smith et al. | 514/824 |

Primary Examiner—Richard L. Raymond
Assistant Examiner—Mark W. Russell
Attorney, Agent, or Firm—Imre (Jim) Balogh; James A. Nicholson

[57] ABSTRACT

Disclosed are novel 3-hydroxy-3-methylglutaryl-coenzyme A reductase inhibitors useful as antihypercholesterolemic agents represented by the formula

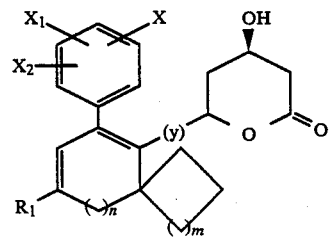

and the corresponding ring-opened hydroxy acids and esters derived therefrom and pharmaceutically acceptable salts thereof.

Pharmaceutical compositions containing said compounds and method of inhibiting the biosynthesis of cholesterol therewith are also disclosed.

21 Claims, No Drawings

NOVEL HMG-COA REDUCTASE INHIBITORS

BACKGROUND OF THE INVENTION

This application is a continuation-in-part application of U.S. patent application Ser. No. 135,805, filed Dec. 21, 1987 now U.S. Pat. No. 4,863,957.

1. FIELD OF THE INVENTION

The present invention relates to compounds, pharmaceutical compositions and a method useful for reducing serum cholesterol in humans. More particularly, the invention relates to trans-6-[(2-aryl substituted spirocyclic-1,3-dien-1-yl)alkenyl or alkyl]-3,4,5,6-tetrahydro-4-hydroxy-2H-pyran-2-ones, the corresponding ring opened hydroxy acids and esters derived therefrom and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. RELATED PRIOR ART

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 November (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]-4-hydroxypyran-2-ones useful as hypocholesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphthyl-1')ethyl]-4(R)-hydroxy-3,4,5,6-tetrahydro-2H-pyran-2-ones for inhibition of biosynthesis of cholesterol.

U.S. Pat. No. 4,567,289 to Willard et al. relates to methyl, ethyl, n-propyl,2-(acetylamino)ethyl, or 1-(2,3-dihydroxy)propyl ester of E-(3R,5S)-7-(4'-fluoro-3,3',5-trimethyl-[1,1'-byphenyl]-2-yl)-3,5-dihydroxy-6-heptenoic acid that are HMG-CoA reductase inhibitors.

U.S. Pat. No. 4,611,067 to Volante et al. discloses a process for the preparation of HMG-CoA reductase inhibitors which contain a 4-hydroxy-3,4,5,6-tetrahydro-2H-pyran-2-one moiety.

SUMMARY OF THE INVENTION

In accordance with the present invention, certain trans-6-[(2-aryl substituted spirocyclic-1,3-dien-1-yl)alkenyl or alkyl]-3,4,5,6-tetrahydro-4-hydroxy-2H-pyran-2-ones, the corresponding ring opened hydroxy acids and esters derived therefrom and pharmaceutically acceptable salts thereof are provided which are potent inhibitors of HMG-CoA reductase. Specifically, the invention provides compounds of formula I:

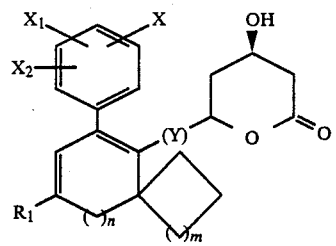

wherein

Y is: —CHR—, —CHRCHR—, —CHRCHRCHR—, or —RC=CR—, wherein R is H or lower alkyl;

$X$, $X_1$ and $X_2$ are independently:
H,
F,
Cl,
Br,
OH,
$CF_3$,
alkyl, or
alkoxy;

$R_1$ is:
H,
alkyl,
substituted alkyl,
cycloalkyl having up to 7 carbon atoms,
$CF_3$, or
aryl;

m is:
0, 1, 2 or 3;

n is:
0 or 1;

its hydroxy acids and esters; and pharmaceutically acceptable salts thereof.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight- or branched-chained containing from 1 to 4 carbon atoms.

"Alkyl" means a saturated or unsaturated aliphatic hydrocarbon which may be either straight- or branched-chained containing from about 1 to 10 carbon atoms; "substituted alkyl" means "halogen", "hydroxy", "alkoxy" or "amino" substitution.

"Alkoxy" means an alkyl oxy group in which "alkyl" is as previously defined. Lower alkoxy groups are preferred which include methoxy, ethoxy, n-propoxy, i-propoxy, sec-propoxy, and n-butoxy.

"Aryl" means an aromatic hydrocarbon radical having 4 to 10 carbon atoms. The preferred aryl groups are phenyl, substituted phenyl and naphthyl. The term "substituted" means "alkyl", "alkoxy", "halogen" or "hydroxyalkyl" substitution.

"Halogen" means chloride, fluoride, bromide and iodide.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and steroisomers of the compounds and mixtures thereof defined by the structural formula.

The general procedures for producing the compounds of the present invention are as follows:

Reaction Sequence I

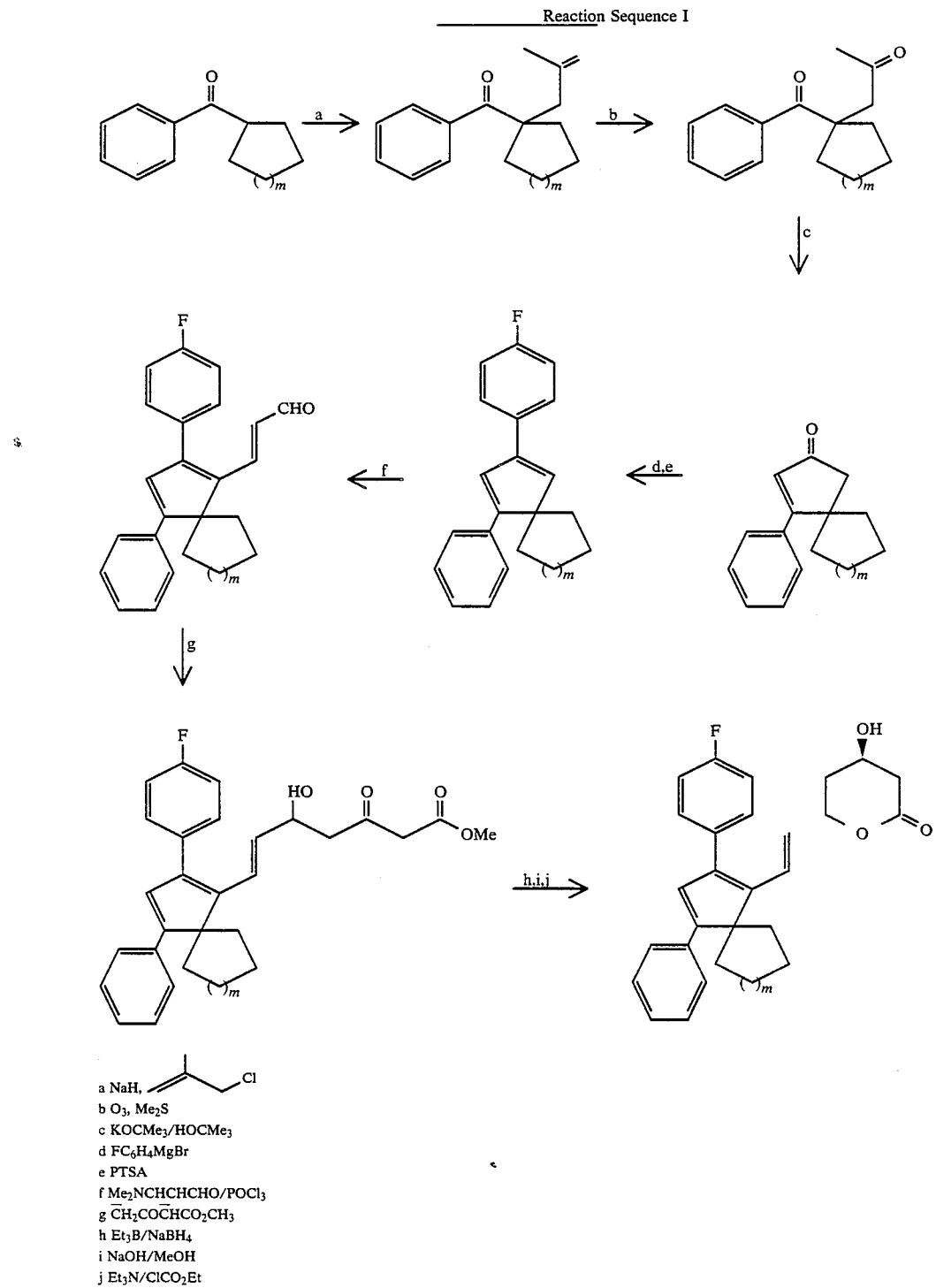

a NaH, <span>/\\/Cl</span>
b O₃, Me₂S
c KOCMe₃/HOCMe₃
d FC₆H₄MgBr
e PTSA
f Me₂NCHCHCHO/POCl₃
g C̄H₂COC̄HCO₂CH₃
h Et₃B/NaBH₄
i NaOH/MeOH
j Et₃N/ClCO₂Et

Reaction Sequence II

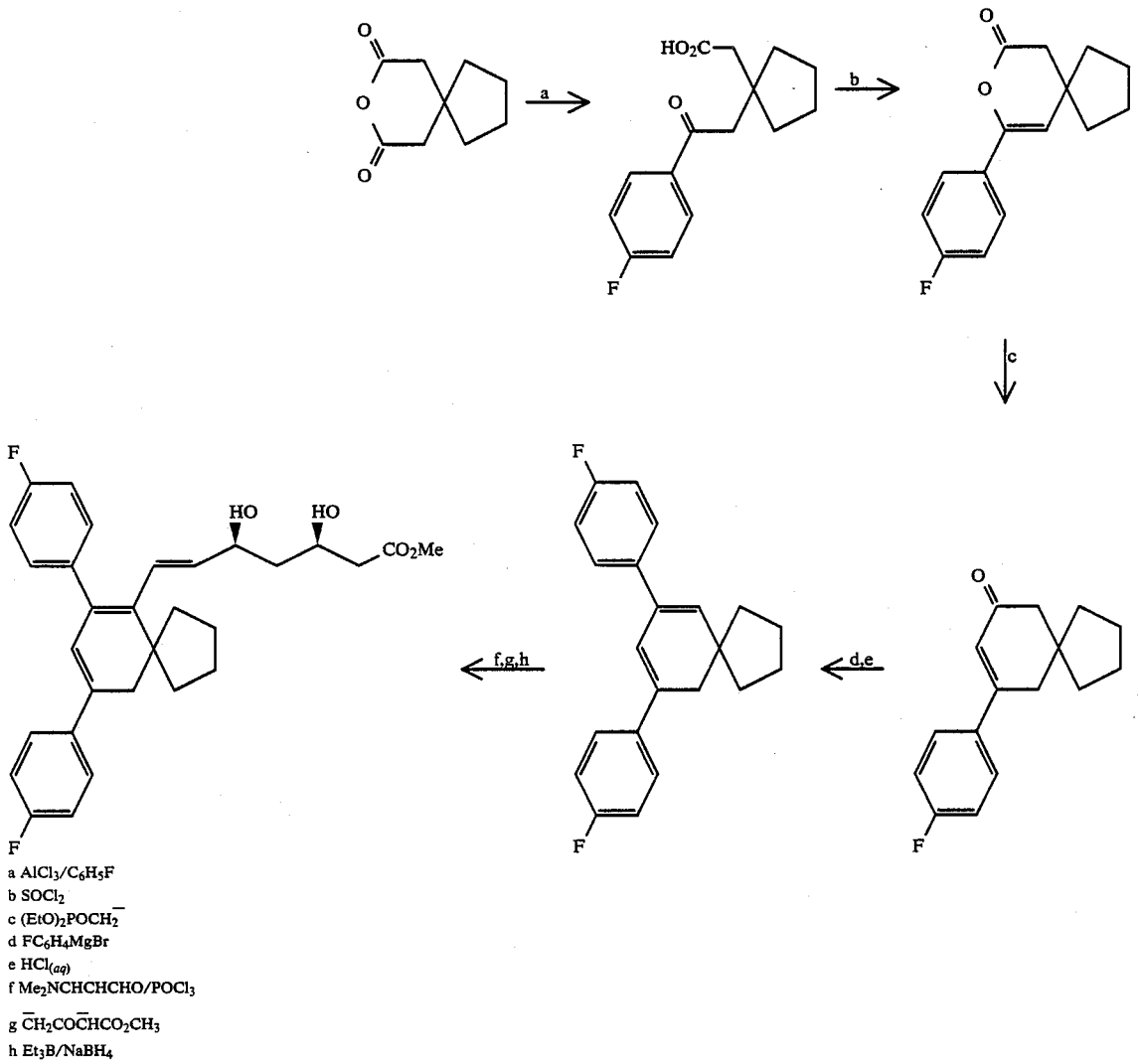

a AlCl$_3$/C$_6$H$_5$F
b SOCl$_2$
c (EtO)$_2$POCH$_2^-$
d FC$_6$H$_4$MgBr
e HCl$_{(aq)}$
f Me$_2$NCHCHCHO/POCl$_3$
g $\overline{\text{CH}_2}$CO$\overline{\text{C}}$HCO$_2$CH$_3$
h Et$_3$B/NaBH$_4$ The starting materials were obtained from the Aldrich Chemical Co. but they may also be synthesized in accordance with methods known in the art.

The following preparative example will further illustrate the invention.

EXAMPLE I

Step 1:
4-Methyl-1-phenyl-2,2-tetramethylene-4-penten-1-one

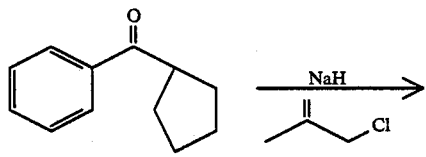

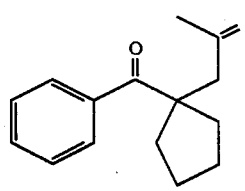

A mixture of 3.6 g (150 mmoles) of mineral oil free sodium hydride, 17.19 ml (100 mmoles) of cyclopentylphenyl ketone, 1.12 g (10 mmoles) of potassium t-butoxide, 15.11 ml (150 mmoles) of 3-Chloro-2-methylpropene, and 100 ml of 1,2-dimethoxyethane was stirred 1 week at room temperature.

The mixture was slowly poured into water and extracted with ether. The organic layer was extracted with brine and the ether removed in vacuo.

Step 2: 1-Phenyl-2,2-tetramethylenepentane-1,4-dione

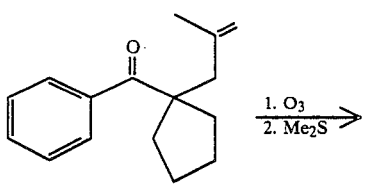

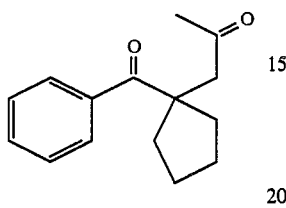

Ozone was bubbled into a cold (−78° C.) solution of the product obtained in Step 1 in 400 ml of ethanol. After approximately 1 hour the reaction developed a blue color. The excess ozone was bubbled out of the reaction with nitrogen gas. The reaction was warmed to 0° C. and the ozonide decomposed with 9.18 ml (125 mmoles) of methyl sulfide.

After stirring overnight at room temperature, the ethanol was removed in vacuo. The residue was redissolved in ether and extracted with H$_2$O, 10% NaHSO$_3$ and brine.

Step 3: 1-Phenyl-spiro[4.4]nona-1-ene-3-one

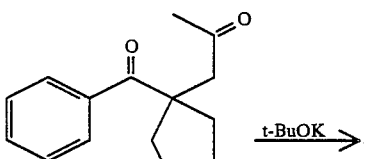

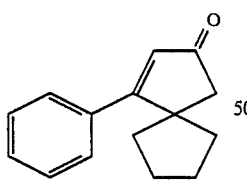

The diketone obtained in Step 2 was dissolved in 100 ml of t-butanol and treated with 12.34 g (110 mmoles) of potassium t-butoxide. After stirring for 2 hours at room temperature, the reaction was neutralized with 10 ml of 12N HCl. The solvent was removed in vacuo and the residue was redissolved in ether and water. The layers were separated and the ether was extracted with brine and dried over MgSO$_4$. After removing the ether in vacuo, the residue was crystallized from an ether/hexane mixture.

White crystals were obtained having an m.p. of 75°–76° C.

Step 4: 3-(4-Fluorophenyl)-1-phenyl-spiro[4.4]nona-1,3-diene

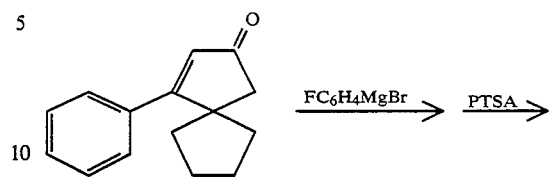

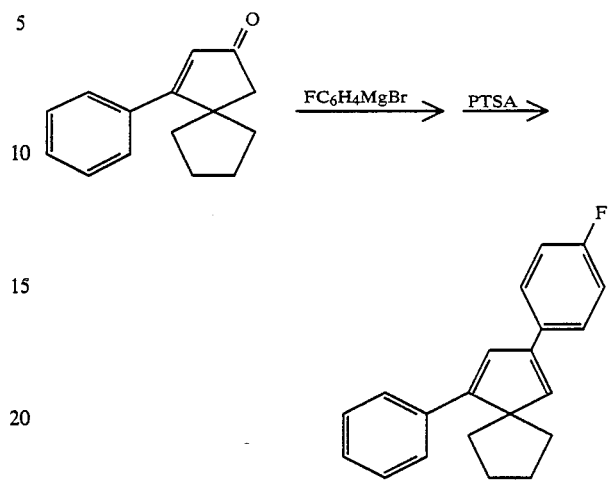

A 1.0M THF solution of the ketone prepared in Step 3 (6.36 g, 30 mmoles) was added dropwise to 20 ml of a 2M THF solution of 4-fluorophenylmagnesium bromide. After stirring 2 hours at room temperature, the reaction was poured into a mixture of ice and 1N HCl. Extraction with ether and evaporation of the solvents gave the crude alcohol.

The alcohol was treated with a catalytic amount of p-toluene sulfonic acid monohydrate (0.57 g, 3 mmoles) in refluxing toluene for 5 minutes to dehydrate the alcohol.

Step 5: (E)-3-[2-(4-fluorophenyl)-4-phenyl-spiro[4.4]nona-1,3-dien-1-yl]2-propenaldehyde

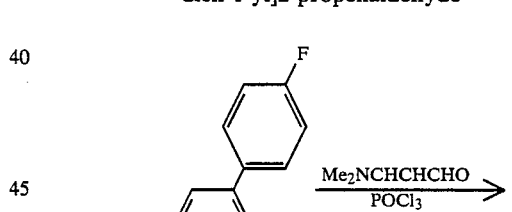

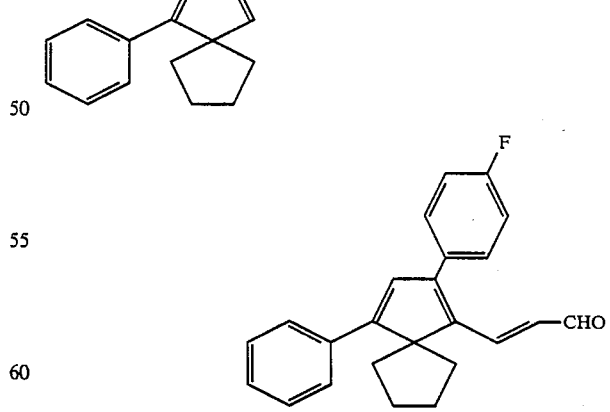

A 2.0M acetonitrile solution of 3-dimethylaminoacrolien (2.97 g, 30 mmoles) was added dropwise to an ice cold acetonitrile solution of POCl$_3$ (3.03 ml, 32.5 mmoles). To this solution, after stirring 15 minutes at 0° C., was added dropwise a 1.0M acetonitrile solution of the diene prepared in step 4 (7.25 g, 25 mmoles). The reaction mixture was warmed to room temperature and stirred for 25 hours. The dark reaction mixture was poured into 100 ml of 2N NaOH and stirred for 10 minutes. The resulting mixture was extracted with ethyl acetate.

The organic layer was extracted with brine and the solvents removed in vacuo. The residue was redissolved in hexane and placed in the freezer (−20° C.) overnight. The hexane was filtered to yield 3.9 g (11.34 mmoles) of a tan-colored solid.

Step 6:
Methyl-(E)-7-[2-(4-fluorophenyl)-4-phenyl-spiro[4.4]-nona-1,3-dien-1-yl]-5-hydroxy-3-oxo-6-heptenoate ane solution of n-butyllithium. After 15 minutes, when the temperature had warmed to −40° C., 1.30 ml (12 mmoles) methylacetoacetate was added dropwise. The solution was stirred for 30 minutes while the temperature was allowed to warm to −10° C.

To the yellow solution of the dianion was added a 0.25M THF solution of 3.44 g (10 mmoles) of the aldehyde prepared in Step 5. The addition took 30 minutes. The reaction was stirred an additional 30 minutes at −10° C., then poured into ethyl acetate and extracted with H₂O, saturated NaHCO₃ and brine.

The residue was purified by flash chromatography on silica gel with hexane/ethyl acetate (5/1) as the eluent.

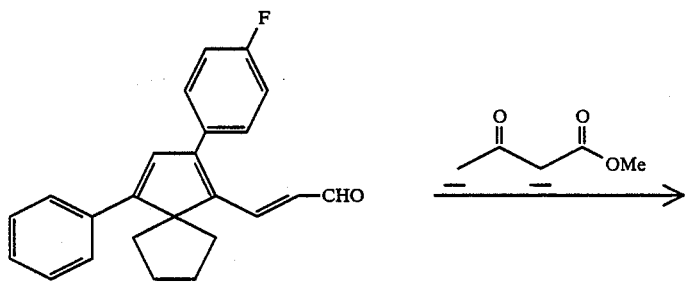

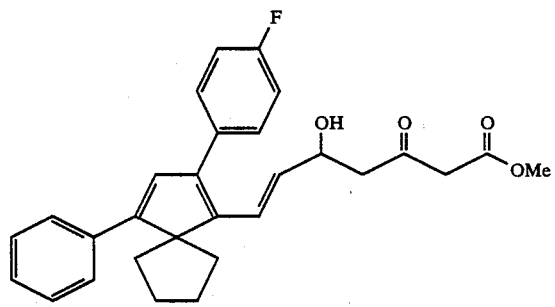

To a stirred solution of diisopropyl amine (4.03 ml, 28.8 mmoles), in 58 ml of THF, at −60° C., under nitrogen, was added 10.56 ml (26.4 mmoles) of a 2.5M hex- Step 7:
Methyl-(E)-7-[2-(4-fluorophenyl)-4-phenyl-spiro[4.4]-nona-1,3-dien-1-yl]-3,5-dihydroxy-6-heptenoate

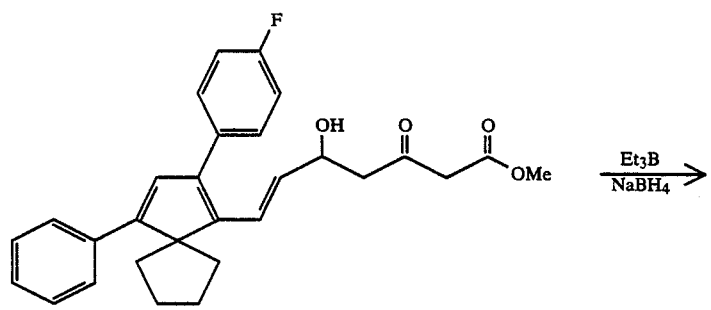

-continued

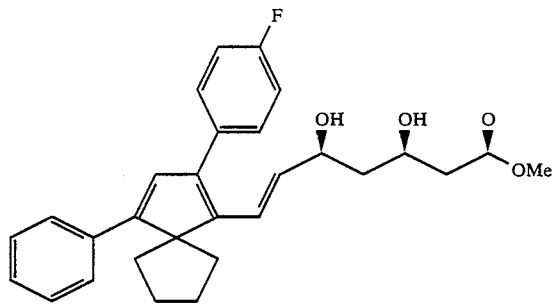

The 5-hydroxy-3-keto ester (4.1 g 8.91 mmoles) prepared in Step 6 was dissolved in 22 ml of dry THF and treated with triethylborane (1M in THF, 13.4 ml, 13.4 mmoles). After stirring for 5 minutes at room temperature, the reaction mixture was cooled to −78° C. Sodium borohydride (0.40 g, 10.7 mmoles) was added, followed by dropwise addition of methanol (8.9 ml) over a 30 minute period. The reaction was stirred for 30 minutes at −78° C. and over the next 30 minutes was allowed to warm to −60° C. At −60° C. the reaction was quenched by the dropwise addition of 30% $H_2O_2$ (20 ml) in $H_2O$ (50 ml).

The reaction was warmed to room temperature and stirred for 30 minutes. It was poured into ethyl acetate and extracted with dilute $NH_4Cl$ solution. The organic layer was extracted with saturated $NaHCO_3$ and brine.

Step 8:
(E)-7-[2-(4-fluorophenyl)-4-phenyl-spiro[4.4]nona-1,3-dien-1-yl]-3,5-dihydroxy-6-heptenoic acid

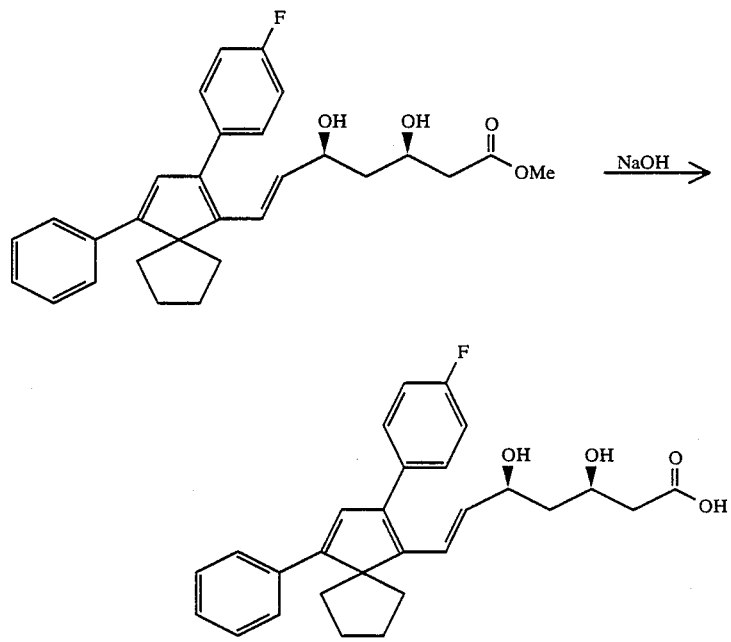

Aqueous 1N NaOH (13.4 ml, 13.4 mmoles) was added to a 0.2M ethanol solution of the 3,5-dihydroxy ester prepared in Step 7 (4.1 g, 8.9 mmoles). After stirring for 10 minutes, the ethanol was evaporated in vacuo. The residue was redissolved in $H_2O$ and the aqueous layer was acidified with 1N HCl (15 ml, 15 mmoles).

The aqueous layer was extracted with ether. The ether layer was extracted with brine and dried over $Na_2SO_4$. After filtration, the ether was removed in vacuo.

Step 9:
Trans-(E)-6-[2-[2-(4-fluorophenyl)-4-phenyl-spiro[4.4]-nona-1,3-dien-1-yl]ethenyl]-3,4,5,6-tetrahydro-2H-pyran-2-one

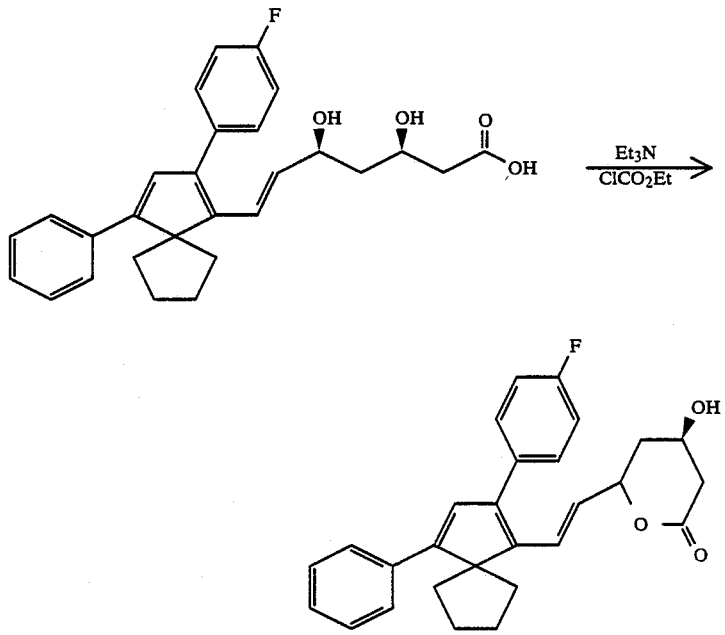

A 1.0M H₂CCl₂ solution of ethyl chloroformate (0.76 ml, 8 mmoles) was added dropwise to a cold (−10° C.) 0.2M H₂CCl₂ solution of 3.6 g (8 mmoles) of the 3,5-dihydroxycarboxylic acid prepared in Step 8 and 1.34 ml (9.6 mmoles) of triethylamine. The reaction was stirred for 15 minutes at −10° C., then poured into H₂O. The layers were separated and the H₂CCl₂ layer extracted with saturated NaHCO₃.

The H₂CCl₂ was removed in vacuo and the residue chromatographed on silica gel using 1/1 ethylacetate/hexane as the eluent. The resulting compound was recrystallized from H₂CCl₂/hexane to give a tan-colored solid having an m.p. of 124°–5° C. (dec).

Elemental analysis: calc C 78.12; H 6.32, found C 78.01; H 6.33.

Employing the general method detailed in Example I the following compounds can be prepared:
1. trans-(E)-6-[2-[2-(4-fluoro-3-methylphenyl)-4-phenyl-spiro-[4.4]-nona-1,3-dien-1-yl]ethenyl]-3,4,5,6-tetrahydro-2H-pyran-2-one;
2. trans-(E)-6-[2-[7,9-di-(4-fluorophenyl)-spiro[4.5]-]deca-6,8-dien-6-yl]ethenyl]-3,4,5,6-tetrahydro-2H-pyran-2-one;
3. trans-(E)-6-[2-[2-(4-fluorophenyl)-4-(4-hydroxymethylphenyl)spiro[4.5]deca-1,3-dien-1-yl]ethenyl]-3,4,5,6-tetrahydro-2H-pyran-2-one;
4. trans-(E)-6-[2-[6-(4-fluoro-3-methylphenyl)-8-(cyclohexyl)-spiro[3.5]nona-5,7-dien-5-yl]ethenyl]-3,4,5,6-tetrahydro-2H-pyran-2-one;
5. trans-(E)-6-[2-[2-(4-fluorophenyl)-4-(6-hexanol)-spiro[4.4]-nona-1,3-dien-1-yl]ethenyl]-3,4,5,6-tetrahydro-2H-pyran-2-one: and
6. trans-(E)-6-[2-[5-(4-fluorophenyl)-7-(2-hydroxyprop-2-yl)-spiro[2.4]hepta-4,6-dien-4-yl]ethenyl]-3,4,5,6-tetrahydro-2H-pyran-2-one.

EXAMPLE II

Step 1:
3,3-Tetramethylene-5-oxo-5-(4-fluorophenyl)pentanoic acid

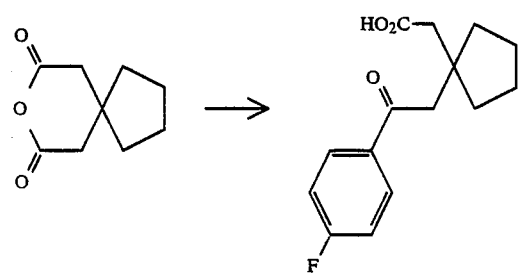

Solid 3,3-tetramethyleneglutaric anhydride (25.22 g, 150 mmoles) was added portionwise to a stirred mixture of 40 g (300 mmoles) of AlCl₃ in 125 ml of fluorobenzene. After stirring for 2 hours at room temperature, the thick reaction mixture was added portionwise to 500 ml of ice water. The mixture was extracted with 1L of ether and the organic layer was extracted with water. After drying over MgSO₄ the ether was evaporated in vacuo. The gummy residue was used directly in the next step without purification.

Step 2:
3,4-Dihydro-4,4-tetramethylene-6-(4-fluorophenyl)2H-pyran-2-one

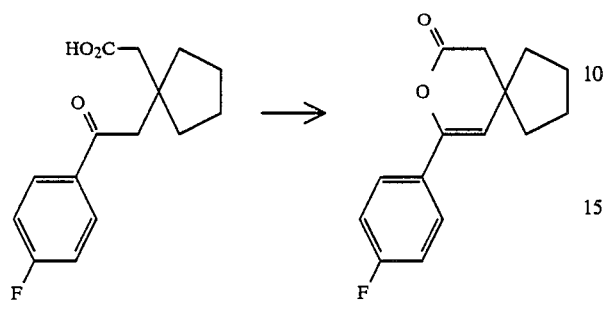

Thionyl chloride (150 ml) was added to the product prepared in Step 1. The reaction mixture was heated to reflux for 10 minutes to give a solution. After cooling, the excess thionyl chloride was removed in vacuo. The residue was redissolved in ether and extracted with water, saturated $NaHCO_3$ and brine. After drying over $MgSO_4$, the ether was removed in vacuo and the residue stirred with 250 ml of hexane to give 18.3 g of a tan-colored solid having an m.p. of 55°–7° C.

Step 3: 9-(4-Fluorophenyl)spiro[4.5]deca-8-ene-7-one

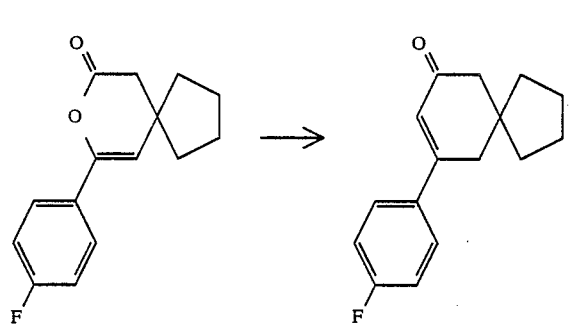

A 2.0M THF solution of diethylmethylphosphonate (4.63 g, 30.46 mmoles) was added dropwise to a cold (−78° C.) solution of n-butyllithium (12.79 ml of a 2.5M hexane solution, 31.98 mmoles) in 75 ml of THF. After stirring for 15 minutes at −78° C., a solution of the lactone, prepared in Step 2 (7.5 g, 30.46 mmoles), in 20 ml of THF was added dropwise. The reaction was warmed to room temperature and stirred for 16 hours. The reaction mixture was poured into 300 ml of water and extracted with ether.

The organic layer was extracted with brine and the solvents removed in vacuo. The compound was purified by chromatography on silica gel with hexane/ethylacetate (10/1) as the eluent to yield 1.8 g of product.

Step 4: 7,9-Di-(4-fluorophenyl)spiro[4,5]deca-6,8-diene

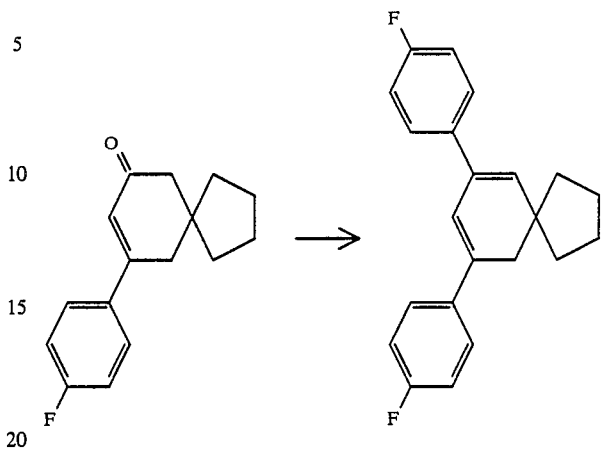

To an ice cold, 1M THF solution of 4-fluorophenyl-magnesium bromide (50 ml, 50 mmoles) was added a 0.3 g, 32.75 mmoles). The mixture was stirred at room temperature for 15 hours and then poured into 250 ml of cold 1N HCl. The mixture was stirred at room temperature for 30 minutes, then extracted with ether. The ether was evaporated in vacuo and the residue chromatographed on silica gel with hexane as the eluent to yield 4.5 g of the diene.

Step 5:
(E)-3-[7,9-di-(4-fluorophenyl)spiro[4.5]deca-6,8-dien-6-yl]2-propenaldehyde

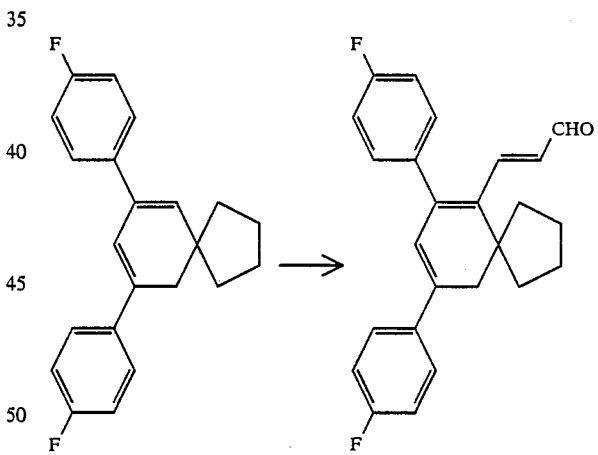

To a solution of phosphorus oxychloride (1.69 ml, 18.15 mmoles) in 50 ml of acetonitrile cooled in an ice bath was added 3-dimethylaminoacrolein (1.68 ml, 16.75 mmoles) dropwise over 3 minutes. The mixture was stirred for 5 minutes and a solution of 7,9-di-(4-fluorophenyl)spiro[4.5]deca-6,8-diene (4.5 g, 13.96 mmoles) in 150 ml of warm acetonitrile was added dropwise over 30 minutes. The mixture was stirred at room temperature for 16 hours and was then heated in an oil bath at 60° C. for 6 hours. The mixture was cooled and poured into 400 ml of cold 1N sodium hydroxide. The mixture was extracted with ether. The ether was washed with water and evaporated in vacuo. The residue was triturated with 17.5 ml of boiling hexane and was filtered. The filtrate, upon cooling in the freezer overnight, deposited 2.7 g of product having an m.p. of 120°–4° C.

Step 6:
Methyl-(E)-7-[7,9-di-(4-fluorophenyl)spiro[4.51]deca-6,8-dien-6-yl]-5-hydroxy-3-oxo-6-heptenoate

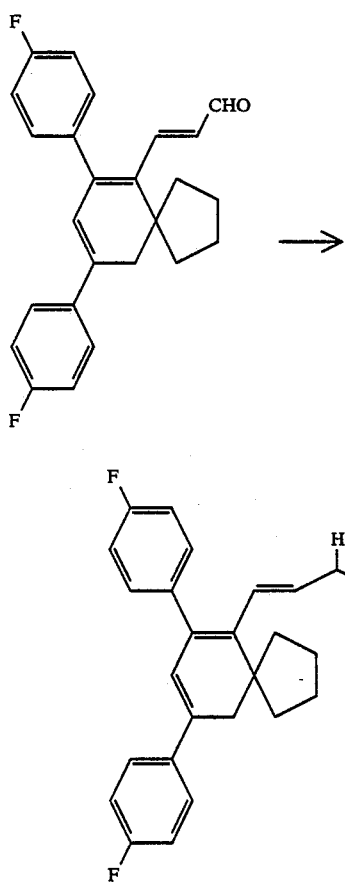

To a stirred solution of diisopropylamine (3.13 ml, 22.38 mmoles) in 80 ml of anhydrous THF at −78° C., under nitrogen, was added 8.24 ml (20.59 mmoles) of a 2.5M hexane solution of n-butyllithium. After stirring for 5 minutes, a solution of methyl acetoacetate (1.07 g, 9.19 mmoles) in 10 ml of THF was added dropwise over 15 minutes. The dry ice - acetone bath was removed and, after 10 minutes, an ice bath was applied. The mixture was stirred for 1.5 hours. To this mixture was added a solution of (E)-3-[7,9-di-(4-fluorophenyl)-spiro[4.5]deca-6,8-dien-6-yl]2-propenaldehyde (2.7 g, 7.17 mmoles) in 50 ml of THF dropwise over 40 minutes. The mixture was stirred in ice for 1 hour and a solution of glacial acetic acid (2.46 ml, 42.97 mmoles) in 10 ml of THF was added dropwise over 5 minutes. The mixture was poured into 250 ml of ethylacetate and was extracted with water, sodium bicarbonate and brine. The organic layer was dried over magnesium sulfate and was evaporated in vacuo to give 3.3 g of product having an m.p. of 96°–9° C.

Step 7:
Methyl-(E)-7-(7,9-di-(4-fluorophenyl)spiro[4.5]deca-6,8-dien-6-yl]-3,5-dihydroxy-6-heptenoate

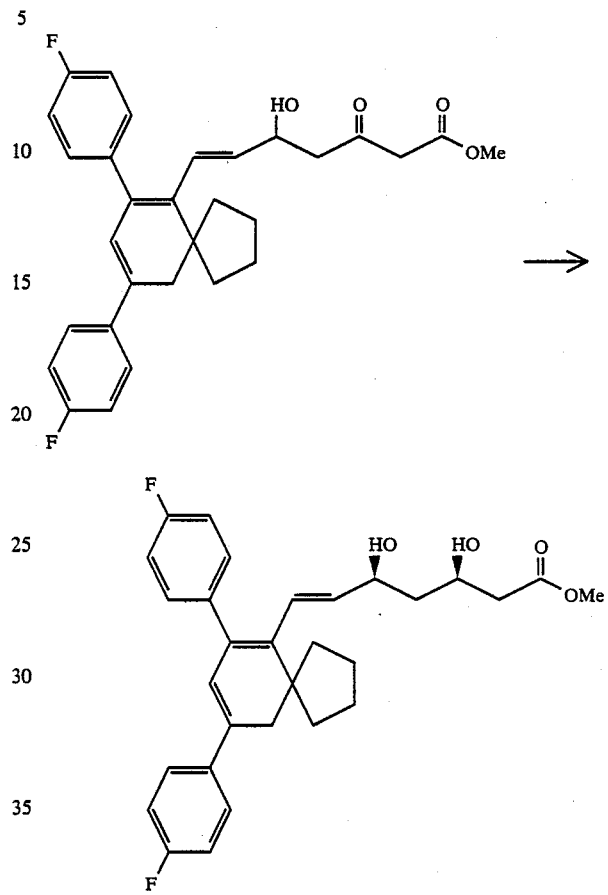

To a solution of methyl-(E)-7-[7,9-di-(4-fluorophenyl)spiro-[4.5]deca-6,8-dien-6-yl]-5-hydroxy-3-oxo-6-heptenoate (3.0 g, 6.09 mmoles) in 80 ml of anhydrous THF was added a 1M THF solution of triethylborane (9.07 ml, 9.07 mmoles). The solution was stirred for 5 minutes at room temperature and was then cooled to −78° C. in a dry ice−acetone bath. To this mixture was added sodium borohydride (0.27 g, 7.0 mmoles) followed by the dropwise addition over 30 minutes of a solution of 6.09 ml of methanol in 15 ml of THF. The reaction was stirred for 1 hour with the temperature slowly rising to −50° C. To this mixture was added a solution of 30% hydrogen peroxide (14.17 ml) in water (7 ml) dropwise over 5 minutes. The reaction was stirred at room temperature for 1 hour and was poured into 200 ml of ethyl acetate. The mixture was extracted with 1N HCl and then brine. The organic layer was evaporated in vacuo to give 2.8 g of material. The residue was dissolved in ethyl acetate and the solution was diluted with hexane to precipitate a solid product having an m.p. of 113°–15° C. (dec).

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test methods described hereunder. The methods are based on the articles: "Purification of 3-hydroxy-3-methylglutarylcoenzyme A reductase from rat liver" by Kleinsek et al., Proc. Natl. Acad. Sci. U.S.A., Vol. No. 4, pp. 1431–1435, April 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. U.S.A., Vol 77, pp. 3951–3961, July 1980, Biochemistry; "Effects of ML-236B on cholesterol metabolism in mice rats: Lack of hypocholesterolemic activity in normal animals" by Endo et al., Biochimica et Biophysica Acta, 575 (1979) 266–276; and "Evidence of regulation of 3-hydroxy-3-methylglutaryl coenzyme A reductase activity and cholesterol synthesis in non-hepatic tissues of rat" by Balasubramaniam et al., Proc. Natl. Acad. Sci. U.S.A., Vol. 73, No. 8, pp. 2564–2568, August 1976, Biochemistry.

The first method used (designated HMGR Screen) was as follows. Male rats were acclimated to an alternate 12 hour light-dark cycle for a period of 2-3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 $\mu$l portion samples. Prior to use, the enzyme was activated at 37° C. for 30 minutes in a reaction mixture. The reaction mixture contained in a volume of 240 $\mu$l: 0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG-CoA; 20 $\mu$M HMG-CoA, and 200 $\mu$g of solubilized enzyme with and without inhibitors (in 10 $\mu$l DMSO). After 5 minutes incubation at 37° C. the reaction was initiated with 0.2 mM NADPH. The final assay volume was 300 $\mu$l. The reaction then was terminated with 100 $\mu$l of 1N HCl. After an additional incubation for 15 minutes at 37° C. to allow for complete lactonization of the product, the mixture was diluted with 3 ml GDW. The diluted mixture was then poured over a 0.7 × 1.4 cm column containing 100–200 mesh Bio-Rex ion-exchange resin (cloride form of Bio-Rad) which was equilibrated with distilled water. With this resin the unreacted [$^{14}$C] HMG-CoA was adsorbed and the product [$^{14}$C] lactone was eluted (80% recovery) directly into scintillation vials. After the addition of 10 ml of Aquasol ®, radioactivities of the samples were measured in a scintillation counter. Results on the compound obtained in Example I, Step 9 and on its lactone form are shown in Table I.

The second method (designated Ex-Vivo Fasted) used was as follows. Rats of 170–210 g were maintained on a low cholesterol diet for one week prior to use. Drugs (identified in Table I) were given orally in 0.5% methocel to fasted (fasted for 16 hours) rats. After one hour the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2$\mu$ Ci, 1 mM). The tubes were gassed with 95% $O_2$/5%$CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. Result on the sodium salt of the compound of Example I, Step 9 is shown in Table I.

TABLE I

| | *ID$_{50}$ (Micromoles per liter) or % Cholesterol Inhibition | | |
|---|---|---|---|
| Assay | Compound of Example I Step 9 | Lactone Form of Compound of Example I Step 9 | Sodium Salt of Compound of Example I Step 9 |
| HMGR Screen | .00090 μM | 0.07μM | |
| Ex Vivo Fasted | 1 mg/kg | | 65 ± 4% |

*The micromolar concentration of compound required for 50% inhibition of cholesterol synthesis = IC$_{50}$

What is claimed is:

1. A compound of the formula

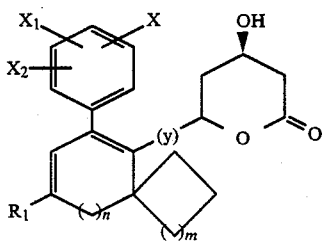

wherein
Y is:
—CHR—,
—CHRCHR—,
—CHRCHRCHR—, or
—RC=CR—, wherein R is H or lower alkyl;
X, $X_1$ and $X_2$ are independently:
H,
F,
Cl,
Br,
OH,
CF$_3$,
alkyl, or
alkoxy;
R$_1$ is:
H,
alkyl,
substituted alkyl,
CF$_3$,
aryl, or
substituted aryl;
m is: 0, 1, 2 or 3; and
n is: 0 or 1.

2. A compound of claim 1 wherein X is fluoro.
3. A compound of claim 1 wherein X is fluoro and R$_1$ is alkyl of 1–6 carbon atoms.
4. A compound of claim 1 wherein R$_1$ is aryl and X is trifluoromethyl.
5. A compound of claim 1 wherein X is alkyl and R$_1$ is phenyl.
6. A compound of claim 1 wherein X is alkyl and R$_1$ is substituted phenyl.
7. A compound of claim 1 wherein X is H and R$_1$ is naphthyl.
8. A compound of claim 1 wherein R is lower alkyl having 1–4 carbon atoms.
9. A compound of claim 1 wherein R$_1$ is fluorophenyl.
10. A compound of claim 1 wherein n is 1.
11. A compound of claim 1 wherein Y is —CH=CH—.
12. A compound of claim 1 wherein Y is —CH$_2$CH$_2$—.
13. Trans-(E)-6-[2-[2-(4-fluoro-3-methylphenyl)-4-phenyl-spiro-[4.4]nona-1,3-dien-1-yl]ethenyl]-3,4,5,6-tetrahydro-2H-pyran-2-one.
14. Trans-(E)-6-[2-[7,9-di-(4-fluorophenyl)-spiro[4.5]deca-6,8-dien-6-yl]ethenyl]-3,4,5,6-tetrahydro-2H-pyran-2-one.
15. Trans-(E)-6-[2-[2-(4-fluorophenyl)-4-(4-hydroxymethylphenyl)spiro[4.5]deca-1,3-dien-1-yl]ethenyl]-3,4,5,6-tetrahydro-2H-pyran-2-one.
16. Trans-(E)-6-[2-[5-(4-fluorophenyl)-7-(2-hydroxyprop-2-yl)-spiro[2.4]hepta-4,6-dien-4-yl]ethenyl]-3,4,5,6-tetrahydro-2H-pyran-2-one.
17. Trans-(E)-6-[2-[2-(4-fluorophenyl)-4-phenyl-spiro[4.4]nona-1,3-dien-1-yl]ethenyl]-3,4,5,6-tetrahydro-2H-pyran-2-one.
18. A hypocholesterolemic, hypolipidemic pharmaceutical composition comprising a therapeutically effective amount of a compound of claim 1 and a pharmaceutically acceptable carrier.
19. The hypocholesterolemic, hypolipidemic pharmaceutical composition of claim 18 wherein said compound is selected from the group consisting of:
trans-(E)-6-[2-[2-(4-fluoro-3-methylphenyl)-4-phenyl-spiro[4.4]nona-1,3-dien-1-yl]ethenyl]-3,4,5,6-tetrahydro-2H-pyran-2-one;
trans-(E)-6-[2-[7,9-di-(4-fluorophenyl)-spiro[4.5]deca-6,8-dien-6-yl]ethenyl]-3,4,5,6-tetrahydro-2H-pyran-2-one; and
trans-(E)-6-[2-[2-(4-fluorophenyl)-4-(4-hydroxymethylphenyl)spiro[4.5]deca-1,3-dien-1-yl]ethenyl]-3,4,5,6-tetrahydro-2H-pyran-2-one.
20. The hypocholesterolemic, hypolipidemic pharmaceutical composition of claim 18 wherein said compound is selected from the group consisting of:
trans-(E)-6-[2-[5-(4-fluorophenyl)-7-(2-hydroxyprop-2-yl)-spiro[2.4]hepta-4,6-dien-4-yl]ethenyl]-3,4,5,6-tetrahydro-2H-pyran-2-one; and
trans-(E)-6-[2-[2-(4-fluorophenyl)-4-phenyl-spiro[4.4-]nona-1,3-dien-1-yl]ethenyl]-3,4,5,6-tetrahydro-2H-pyran-2-one.
21. A method of inhibiting cholesterol biosynthesis in a patient in need of such treatment comprising administering a pharmaceutical composition defined in claim 18.

* * * * *

UNITED STATES PATENT AND TRADEMARK OFFICE
CERTIFICATE OF CORRECTION

PATENT NO. : 4,904,691

DATED : February 27, 1990

INVENTOR(S) : Kent W. Neuenschwander and Anthony C. Scotese

It is certified that error appears in the above-identified patent and that said Letters Patent is hereby corrected as shown below:

In column 13, in each of lines 5, 53, 55, 59, 62, 65 and 68, the portion reading "tetrahydro-2H" should read --tetrahydro-4-hydroxy-2H--;

In column 22, in each of lines 16, 18, 22, 25, 27-28, 37-38, 40, 44, 50 and 52-53, the portion reading "tetrahydro-2H" should read --tetrahydro-4-hydroxy-2H--.

Signed and Sealed this

Twenty-first Day of May, 1991

Attest:

HARRY F. MANBECK, JR.

Attesting Officer

Commissioner of Patents and Trademarks